United States Patent [19]

Krapcho et al.

[11] 4,065,617
[45] Dec. 27, 1977

[54] 2-(2,2,2,-TRIFLUOROETHYL)-3,3A,4,5,6,7-HEXAHYDRO-2H-PYRAZOLO[4,3-C]PYRIDINES

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 765,572

[22] Filed: Feb. 4, 1977

[51] Int. Cl.² .................. C07D 471/02; C07D 471/06
[52] U.S. Cl. .............................. 542/450; 260/293.55
[58] Field of Search ........................ 260/240 F, 293.55

[56] References Cited

U.S. PATENT DOCUMENTS

| | | | |
|---|---|---|---|
| 3,852,279 | 12/1974 | Krapcho et al. | 260/240 F |
| 3,911,129 | 10/1975 | Krapcho et al. | 260/240 F X |
| 3,923,816 | 12/1975 | Krapcho et al. | 260/293.55 |
| 3,931,169 | 1/1976 | Krapcho et al. | 260/240 F |

Primary Examiner—Allen B. Curtis

Attorney, Agent, or Firm—Lawrence S. Levinson; Merle J. Smith; Donald J. Barrack

[57] ABSTRACT

Antiinflammatory activity is demonstrated by compounds having the formula

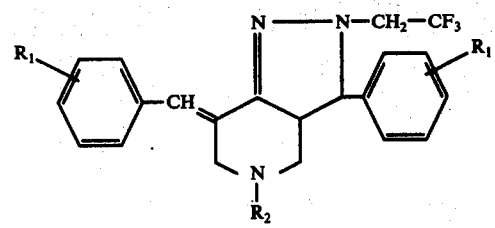

wherein $R_1$ is hydrogen, chloro, fluoro, alkyl, alkoxy or trifluoromethyl and $R_2$ is hydrogen, alkyl, arylalkyl, hydroxyalkyl, or carboximidamide, or pharmaceutically acceptable salts thereof.

14 Claims, No Drawings

2-(2,2,2,-TRIFLUOROETHYL)-3,3A,4,5,6,7-HEXAHYDRO-2H-PYRAZOLO[4,3-C]PYRIDINES

BACKGROUND OF THE INVENTION

Pyrazolo[4,3-c]pyridines are known in the art. More specifically, U.S. Pat. No. 3,852,279 discloses 2-alkyl-7-arylidene-3-aryl-3,3a,4,5,6,7-hexahydropyrazolo[4,3-c]pyridines either unsubstituted in the 5-position or substituted with an alkyl, arylalkyl, hydroxyalkyl, or alkanoyl group; U.S. Pat. No. 3,897,420 discloses 7-arylidene-3-aryl-3,3a,4,5,6,7-hexahydro-2-(substituted aminoalkyl)pyrazolo[4,3-c]pyridines either unsubstituted in the 5-position or substituted with an alkyl, arylalkyl, hydroxyalkyl or alkanoyl group; U.S. Pat. No. 3,911,129 discloses 7-arylidene-3-aryl-5-carboximidamide-2,3,3a,4,6,7-hexahydropyrazolo[4,3-c]pyridines either unsubstituted in the 2-position or substituted with an alkyl, arylalkyl, hydroxyalkyl or alkanoyl group; U.S. Pat. No. 3,923,816 discloses (as intermediates) 7-arylidene-3-aryl-3,3a,4,5,6,7-hexahydropyrazolo[4,3-c]pyridines either unsubstituted in the 2- and 5-positions or substituted with alkyl, hydroxyalkyl, alkanoyl, or arylalkyl groups; U.S. Pat. No. 3,926,968 discloses 5-alkanoylalkyl-7-arylidene-3-aryl-3,3a,4,5,6,7-hexahydropyrazolo[4,3-c]pyridines either unsubstituted in the 2-position or substituted with an alkyl, alkanoyl, hydroxyalkyl or arylalkyl group; and U.S. Pat. No. 3,931,169 discloses 7-arylidene-3-aryl-5-(substituted aminoalkanoyl)-3,3a,4,5,6,7-hexahydropyrazolo[4,3-c]pyridines either unsubstituted in the 2-position or substituted with an alkyl, arylalkyl, hydroxyalkyl or alkanoyl group.

BRIEF DESCRIPTION OF THE INVENTION

Compounds having the formula

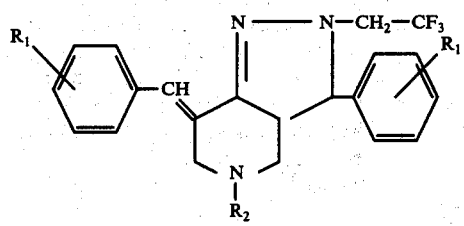

and the pharmaceutically acceptable salts thereof, have anti-inflammatory activity. In formula I, and throughout the specification, the symbols are as defined below.

$R_1$ is hydrogen, chloro, fluoro, alkyl, alkoxy or trifluoromethyl; and $R_2$ is hydrogen, alkyl, arylalkyl, hydroxyalkyl, or carboximidamide

The term "alkyl," as used throughout the specification, refers to straight or branched chain alkyl groups having 1 to 8 carbon atoms.

The term "alkoxy," as used throughout the specification, refers to groups having the formula alkyl—O—, wherein alkyl is as defined above.

The term "aryl," as used throughout the specification (either by itself or as part of a larger group), refers to phenyl or phenyl monosubstituted with a hydrogen, chloro, fluoro, alkyl, alkoxy, or trifluoromethyl group.

DETAILED DESCRIPTION OF THE INVENTION

The compounds of formula I, and the pharmaceutically acceptable salts thereof, are useful for the treatment of inflammation in mammalian species, e.g., rats, dogs, cats, monkeys, etc. Joint tenderness and stiffness (in conditions such as rheumatoid arthritis) are relieved by the above-described compounds.

The compounds of this invention, and the pharmaceutically acceptable salts thereof, can be formulated for use as anti-inflammatory agents according to accepted pharmaceutical practice in oral dosage forms such as tablets, capsules, elixirs or powders, or in injectable form in a sterile aqueous vehicle prepared according to conventional pharmaceutical practice. The compounds of this invention may be administered in amounts of 100 milligrams per 70 kilograms of animal body weight per day to 2 grams per 70 kilograms of animal body weight per day, preferably 100 milligrams per 70 kilograms of animal body weight per day to 1 gram per 70 kilograms of animal body weight per day.

The compounds of this invention can be prepared using as starting materials compounds having the formulas

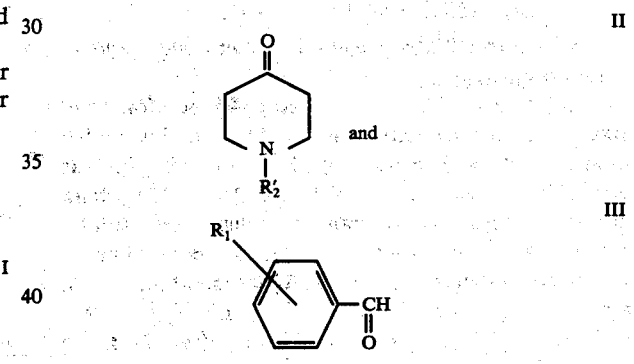

In formula II, and throughout the specification, the symbol $R'_2$ is hydrogen, alkyl, arylalkyl or hydroxyalkyl. Reaction of a 4-piperidone of formula II and an aldehyde of formula III, following the procedure described in the *Journal of the American Chemical Society*, 70:1824 (1948), yields an intermediate having the formula

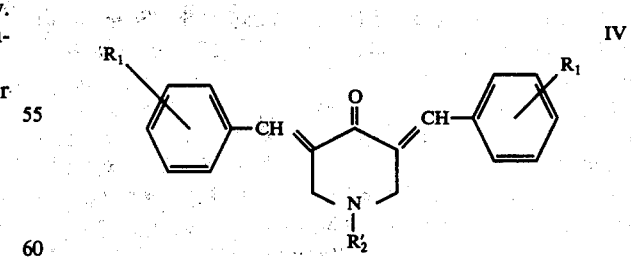

The products of formula I, wherein $R_2$ is other than carboximidamide, can be obtained by reacting an intermediate of formula IV with 2,2,2-trifluoroethylhydrazine. The reaction can be run in an organic solvent, preferably an alcohol of up to four carbon atoms, at an elevated temperature, preferably the reflux temperature of the solvent.

The products of formula I, wherein $R_2$ is carboximidamide can be obtained by reacting the corresponding compound of formula I wherein $R_2$ is hydrogen, with cyanamide in an organic solvent, preferably an alcohol of up to four carbon atoms, at an elevated temperature, preferably the reflux temperature of the solvent.

The compounds of formula I form acid addition salts with inorganic and organic acids. These acid addition salts frequently provide useful means for isolating the intermediates and products described above from reaction mixtures, by forming the salt in a medium in which it is insoluble. The free base may then be obtained by neutralization, and any other salt may then be formed by reaction of the free base with the appropriate acid. Exemplary salts are the hydrohalides (especially the hydrochloride and hydrobromide which are preferred), sulfate, nitrate, phosphate, borate, acetate, tartrate, maleate, citrate, maleate, benzoate, toluenesulfonate and the like.

The following examples are specific embodiments of this invention.

EXAMPLE 1

3,3a,4,5,6,7-Hexahydro-5-methyl-3-phenyl-7-(Phenylmethylene)-2-(2,2,2-trifluoroethyl)-2H-pyrazolo[4,3-c]pyridine, hydrochloride (1:2)

A. 3,5-Dibenzylidene-1-methyl-4-piperidone, hydrochloride

A solution of 57.0 g of 1-methyl-4-piperidone and 106.0 g of benzaldehyde in 400 ml of ethanol is cooled in an ice-bath and treated with hydrogen chloride gas until 250 g is absorbed. The solution is allowed to stand at room temperature for about 16 hours. The resulting solution is seeded, allowed to stand for about 16 hours at room temperature and the crystalline solid filtered on a sintered-glass funnel and washed with cold ethanol and then with ether. After drying in a desiccator, the solid (146 g) is digested in 400 ml of hot ethanol, cooled and filtered to give 120 g of product, melting point 242°-244° C, dec. Recrystallization of 11 g of this material from 35 ml of dimethylformamide gives 9.2 g of product, melting point 242°-244° C, dec.

B. 3,3a,4,5,6,7-Hexahydro-5-methyl-3-phenyl-7-(phenylmethylene)-2-(2,2,2-trifluoroethyl)-2H-pyrazolo[4,3-c]pyridine, hydrochloride (1:2)

A stirred suspension of 12.5 g of 3,5-dibenzylidene-1-methyl-4-piperidone, hydrochloride in 225 ml of methanol is treated with 6.9 g of 70% aqueous 2,2,2-trifluoroethylhydrazine, heated, and the resulting solution refluxed for four hours. The solvent is removed on a rotary evaporator and the light yellow foamy residue (18 g) is dissolved in 90 ml of acetonitrile and treated with 7.5 ml of 5.1 N alcoholic hydrogen chloride; the solid salt rapidly separates after a few seconds. Following cooling for about 16 hours, the material is filtered under nitrogen, washed with cold acetonitrile and ether, and dried in vacuo yielding 9.7 g of material, melting point 185°-187° C (foaming); sintering at 181° C. Crystallization from 50 ml of methanol and 50 ml of ether yields 7.9 g of product, melting point 185°-187° C (foaming).

EXAMPLE 2

3,3a,4,5,6,7-Hexahydro-3-phenyl-7-(phenylmethylene)2-(2,2,2-trifluoroethyl)-2H-pyrazolo[4,3-c]pyridine, hydrochloride (1:1)

A. 3,5-Dibenzylidene-4-piperidone, hydrochloride

A stirred solution of 10 g of 4-piperidone, hydrochloride, hydrate and 14 g of benzaldehyde in 50 ml of ethanol is cooled to 10° C and treated dropwise with 25 ml of concentrated hydrochloric acid (temperature maintained at less than 25° C during the addition) and refluxed for 4 hours; the product begins to separate soon after refluxing begins. After standing at room temperature for about 16 hours, the resulting solid is filtered, washed with cold ethanol and with ether, and air-dried yielding 19.4 g of material, melting point 272°-274° C, dec.

B. 3,3a,4,5,6,7-Hexahydro-3-phenyl-7-(phenylmethylene)-2-(2,2,2-trifluoroethyl)-2H-pyrazolo[4,3-c]pyridine, hydrochloride 3,5-Dibenzylidene-4-piperidone, hydrochloride (10.0g) is reacted with 5.8 g of 70% aqueous 2,2,2-trifluoroethylhydrazine in 220 ml of methanol at reflux for 4 hours. Evaporation of the methanol on a rotary evaporator leaves 14 g of a foamy residue which crystallizes when triturated with 50 ml of boiling acetonitrile to yield (after cooling for about 16 hours) 10.3 g of material, melting point 206°-209° C (sintering at 195° C). Crystallization from 80 ml of ethanol yields 6.7 g of product, melting point 207°-209° C, sintering at 196° C.

EXAMPLE 3

5-Butyl-3,3a,4,5,6,7-hexahydro-3-phenyl-7-(phenylmethylene)-2-(2,2,2,-trifluoroethyl)-2H-pyrazolo[4,3-c]pyridine A. 3,5-Dibenzylidene-1-butyl-4-piperidone, hydrochloride (1:1)

A stirred solution of 31 g of 1-butyl-4-piperidone and 64 g of benzaldehyde in 300 ml of ethanol is cooled to 15° C, treated dropwise with 66 ml of concentrated hydrochloric acid, refluxed for 5 hours, and maintained for about 16 hours at room temperature. The bulk of ethanol is evaporated and the syrupy residue is cooled, diluted to 600 ml with water, treated with 300 ml of ether, stirred, and rubbed; a solid gradually separates. After cooling for several hours, the solid is filtered, washed with ether, and air-dried; yielding 36.7 g of material, melting point 203°-205° C. Following crystallization from 100 ml of dimethylformamide, the material weighs 24.2 g; melting point 212°-214° C.

B. 5-Butyl-3,3a,4,5,6,7-hexahydro-3-phenyl-7-(phenylmethylene)-2-(2,2,2-trifluoroethyl)-2H-pyrazolo[4,3-c]pyridine Ten grams of 3,5-dibenzylidene -1-butyl-4-piperidone, hydrochloride (1:1) and 4.9 g of 70% aqueous 2,2,2-trifluoroethylhydrazine are reacted in 160 ml of methanol for 4 hours at reflux. The solvent is removed on a rotary evaporator yielding 13.6 g of material. When this material is dissolved in 65 ml of acetonitrile and treated with one equivalent of alcoholic hydrogen chloride, only 0.6 g of solid separates on rubbing and cooling for 3 days. Based on the IR spectrum this fraction appears to be the uncyclized hydrazone. Dilution with ether does not precipitate additional material. The solvents are, therefore, evaporated to give 13.7 g of a sticky residue. The residue is shaken with water and ether (the dihydrochloride salt appears to hydrolyze), basified with 5 g of potassium carbonate, the layers separated, the aqueous phase extracted with four portions of ether, the combined extracts dried, and the solvent evaporated to give 10.8 g of a partly solid residue. This is crystallized from 50 ml of isopropyl ether to yield 5.2 g of product, melting point 102°–104° C, sintering at 97° C.

EXAMPLE 4

5-Butyl-3,3a,4,5,6,7-hexahydro-3-phenyl-7-(phenylmethylene)-2-(2,2,2-trifluoroethyl)-2H-pyrazolo[4,3-c]pyridine, maleate salt (1:1)

5-Butyl-3,3a,4,5,6,7-hexahydro-3-phenyl-7-(phenylmethylene)-2-(2,2,2-trifluoroethyl)-2H-pyrazolo[4,3-c]pyridine (5.1 g, see Example 3) and 1.4 g of maleic acid are dissolved in 25 ml of warm acetonitrile and diluted to 400 ml with ether. On seeding and rubbing, the crystalline maleate salt slowly separates. After cooling for about 16 hours, the material is filtered, washed with ether, and dried in vacuo, yielding 4.4 g of material, melting point 150°–155° C (sintering at 130° C). Following crystallization from 15 ml acetonitrile-450 ml ether, the product weighs 3.0 g; melting point 152°–154° C, sintering at 130° C.

EXAMPLE 5

2,3,3a,4,6,7-Hexahydro-3-phenyl-7-(phenylmethylene)-2-(2,2,2-trifluoroethyl)-5H-pyrazolo[4,3-c]pyridine-5-carboximidamide, hydrochloride (1:1)

Ten grams of 3,3a,4,5,6,7-hexahydro-3-phenyl-7-(phenylmethylene)-2-(2,2,2-trifluoroethyl)-2H-pyrazolo[4,3-c]-pyridine, monohydrochloride (see Example 2) is reacted with 8.2 g of cyanamide in 350 ml of ethanol at reflux temperature for 24 hours. The bulk of ethanol is removed on a rotary evaporator and the residue (which does not crystallize) is converted to 10.8 g of the free base (using sodium hydroxide and chloroform extractions); melting point 155°–157° C (foaming), sintering at 120° C. The base is dissolved in 400 ml of dichloromethane, treated with 5 ml of 6.1 N alcoholic hydrogen chloride, and the solvents removed on a rotary evaporator. The foamy residue (11.7 g) is stirred with 50 ml of water and 150 ml of ether. The material becomes gummy, then slowly crystallizes on cooling in ice-water, continued stirring, and rubbing. After standing in the cold for about 16 hours, the product is filtered, washed with ether, and air-dried, yielding 5.3 g of material; melting point 222°–225° C, sintering at 210° C. Crystallization from acetonitrile (dissolved in 200 ml of boiling solvent, then concentrated to approximately 100 ml; crystallization proceeeds very slowly while standing in the cold for several days) yields 3.0 g of product; melting point 230°–232° C, sintering at 223° C.

EXAMPLE 6

3,3a,4,5,6,7-Hexahydro-3-phenyl-5-(2-phenylethyl)-7-(phenylmethylene)-2-(2,2,2-trifluoroethyl)-2H-pyrazolo-[4,3-c]pyridine A. 3,5-Dibenzylidene-1-(2-phenylethyl)-4-piperidone, monohydrochloride Twenty-five grams of 1-(2-phenylethyl)-4-piperidone and 38 g of benzaldehyde are reacted in 180 ml of ethanol in the presence of 40 ml of concentrated hydrochloric acid at reflux temperature for about 5 hours and left at room temperature for about 16 hours yielding 25.5 g of material, melting point 217°–220° C, dec. Crystallization from 50 ml of hot dimethylformamide and 100 ml of acetonitrile yields 22 g of the title compound, melting point 225°–227° C, dec.

B. 3,3a,4,5,6,7-Hexahydro-3-phenyl-5-(2-phenylethyl)-7-(phenylmethylene)-2-(2,2,2-trifluoroethyl)-2H-pyrazolo-[4,3-c]pyridine Ten grams of 3,5-dibenzylidene-1-(2-phenylethyl)-4-piperidone monohydrochloride and 4.4 g of 70% aqueous 2,2,2-trifluoroethylhydrazine are reacted in 150 ml of methanol at reflux for 4 hours. The solvent is removed on a rotary evaporator leaving 13.1 g of brittle residue. The material is converted to 10.7 g of free base using potassium carbonate and ether extractions. The free base is dissolved in 50 ml of warm isopropyl ether and diluted with 20 ml of hexane. After the solution is cooled to room temperature, seeded and rubbed, the crystalline base gradually separates. After cooling overnight, the solid is filtered, washed with cold 5:2 isopropyl ether-hexane and dried to yield 3.6 g of product, melting point 113°–114° C, sintering at 105° C.

EXAMPLE 7

3,3a,4,5,6,7-Hexahydro-3-phenyl-5-(2-phenylethyl)-7-(phenylmethylene)-2-(2,2,2-trifluoromethyl)-2H-pyrazolo[4,3-c]pyridine, maleate salt (1:1)

3,3a,4,5,6,7-Hexahydro-3-phenyl-5-(2-phenylethyl)-7-(phenylmethylene)-2-(2,2,2-trifluoroethyl)-2H-pyrazolo[4,3-c]-pyridine (3.5g) and 0.9 g of maleic acid are dissolved in 20 ml of acetonitrile and diluted to 300 ml with ether. On seeding and rubbing the crystalline maleate salt gradually separates yielding, after cooling for about 16 hours, 3.2 g material, melting point 107°–110° C, sintering at 105° C. Crystallization from methanol-ether yields 2.1 g of product, melting point 108°–110° C, sintering at 106° C.

EXAMPLES 8–14

Following the procedure of Example 1, but substituting the compound listed in column I for 1-methyl-4-piperidone and the compound listed in column II for benzaldehyde, yields the compound listed in column III.

| | Column I | Column II | Column III |
|---|---|---|---|
| 8 | 1-(2-hydroxyethyl)-4-piperidone | 4-methylbenzaldehyde | 3,3a,4,5,6,7-hexahydro-5-(2-hydroxyethyl)-3-(4-methylphenyl)-7-[(4-methylphenyl)methylene]-2-(2,2,2,-trifluoroethyl)-2H-pyrazolo[4,3-c]pyridine |
| 9 | 1-methyl-4-piperidone | 4-methoxybenzaldehyde | 3,3a,4,5,6,7-hexahydro-3-(4-methoxyphenyl)-7-[(4-methoxyphenyl)methylene[-5-methyl-2-(2,2,2-trifluoroethyl)-2H-pyrazolo[4,3-c]pyridine |
| 10 | 1-[2-(4-methylphenyl)ethyl]-4-piperidone | 3-trifluoromethylbenzaldehyde | 3,3a,4,5,6,7-hexahydro-5-[2-(4-methylphenyl)ethyl]-2-(2,2,2-trifluoroethyl)-3-(3-trifluoro- |

-continued

| | Column I | Column II | Column III |
|---|---|---|---|
| 11 | 1-[(4-methoxyphenyl)methyl]4-piperidone | 2-chlorobenzaldehyde | methylphenyl)-7-[3-trifluoromethylphenyl)methylene]-2H-pyrazolo[4,3-c]pyridine 3-(2-chlorophenyl)-7-[(2-chlorophenyl)methylene]-3,3a,4,5,6,7-hexahydro-5-[(4-methoxyphenyl)methyl]-2-(2,2,2-trifluoroethyl)-2H-pyrazolo[4,3-c]pyridine |
| 12 | 1-[4-(3-trifluoromethylphenyl)-butyl]-4-piperidone | 2-fluorobenzaldehyde | 3-(2-fluorophenyl)-7-[(2-fluorophenyl)methylene]-3,3a,4,5,6,7-hexahydro-2-(2,2,2-trifluoroethyl)-5-[4-(3-trifluoromethylphenyl)-butyl]-2H-pyrazolo[4,3-c]pyridine |
| 13 | 4-piperidone | 4-ethylbenzaldehyde | 3-(4-ethylphenyl)-7-[(4-ethylphenyl)methylene]-3,3a,4,5,6,7-hexahydro-2-(2,2,2-trifluoroethyl)-2H-pyrazolo[4,3-c]pyridine |
| 14 | 4-piperidone | 4-ethoxybenzaldehyde | 3-(4-ethoxyphenyl)-7-[(4-ethoxyphenyl)methylene]-3,3a,4,5,6,7-hexahydro-2-(2,2,2-trifluoroethyl)-2H-pyrazolo[4,3-c]pyridine |

EXAMPLES 15–16

Following the procedure of Example 5, but substituting the compound listed in column I for 3,3a,4,5,6,7-hexahydro-3-phenyl-7-(phenylmethylene)-2-(2,2,2-trifluoroethyl)-2H-pyrazolo[4,3-c]pyridine, monohydrochloride, yields the compound listed in column II.

| | Column I | Column II |
|---|---|---|
| 15 | 3-(4-ethylphenyl)-7-[(4-ethylphenyl)methylene]-3,3a,4,5,6,7-hexahydro-2-(2,2,2-trifluoroethyl)-2H-pyrazolo[4,3-c]pyridine, hydrochloride | 3-(4-ethylphenyl)-7-[(4-ethylphenyl)methylene]-2,3,3a,4,6,7-hexahydro-2-(2,2,2-trifluoroethyl)-5H-pyrazolo[4,3-c]pyridine-5-carboximidamide, hydrochloride |
| 16 | 3-(4-ethoxyphenyl)-7-[(4-ethoxyphenyl)methylene]-3,3a,4,5,6,7-hexahydro-2-(2,2,2-trifluoroethyl)-2H-pyrazolo[4,3-c]pyridine, hydrochloride | 3-(4-ethoxyphenyl)-7-[(4-ethoxyphenyl)methylene]-2,3,3a,4,6,7-hexahydro-2-(2,2,2-trifluoroethyl)-5H-pyrazolo[4,3-c]pyridine-5-carboximidamide, hydrochloride |

What is claimed is:
1. A compound having the formula

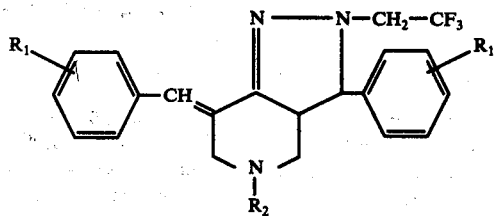

or a pharmaceutically acceptable salt thereof, wherein $R_1$ is hydrogen, chloro, fluoro, alkyl, alkoxy or trifluoromethyl; and $R_2$ is hydrogen, alkyl, arylalkyl, hydroxyalkyl or carboximidamide; and wherein the term aryl refers to phenyl or phenyl monosubstituted with a hydrogen, chloro, fluoro, alkyl, alkoxy or trifluoromethyl group and the terms alkyl and alkoxy refer to groups having 1 to 8 carbon atoms.

2. A compound in accordance with claim 1 wherein $R_2$ is hydrogen.

3. A compound in accordance with claim 1 wherein $R_2$ is alkyl.

4. A compound in accordance with claim 1 wherein $R_2$ is arylalkyl.

5. A compound in accordance with claim 1 wherein $R_2$ is hydroxyalkyl.

6. A compound in accordance with claim 1 wherein $R_2$ is carboximidamide.

7. A compound in accordance with claim 1 wherein $R_1$ is hydrogen.

8. The compound in accordance with claim 1 having the name 3,3a,4,5,6,7-hexahydro-5-methyl-3-phenyl-7-(phenylmethylene)-2-(2,2,2-trifluoroethyl)-2H-pyrazolo[4,3-c]pyridine, hydrochloride (1:2).

9. The compound in accordance with claim 1 having the name 3,3a,4,5,6,7-hexahydro-3-phenyl-7-(phenylmethylene)-2-(2,2,2-trifluoroethyl)-2H-pyrazolo[4,3-c]pyridine, hydrochloride (1:1).

10. The compound in accordance with claim 1 having the name 5-butyl-3,3a,4,5,6,7-hexahydro-3-phenyl-7-(phenylmethylene)-2-(2,2,2-trifluoroethyl)-2H-pyrazolo[4,3-c]-pyridine.

11. The compound in accordance with claim 1 having the name 5-butyl-3,3a,4,5,6,7-hexahydro-3-phenyl-7-(phenylmethylene)-2-(2,2,2-trifluoroethyl)-2H-pyrazolo[4,3-c]pyridine,maleate (1:1).

12. The compound in accordance with claim 1 having the name 2,3,3a,4,6,7-hexahydro-3-phenyl-7-(phenylmethylene)-2-(2,2,2-trifluoroethyl)-5H-pyrazolo[4,3-c]pyridine-5-carboximidamide, hydrochloride (1:1).

13. The compound in accordance with claim 1 having the name 3,3a,4,5,6,7-hexahydro-3-phenyl-5-(2-phenylethyl)-7-(phenylmethylene)-2-(2,2,2-trifluoroethyl)-2H-pyrazolo-[4,3-c]pyridine.

14. The compound in accordance with claim 1 having the name 3,3a,4,5,6,7-hexahydro-3-phenyl-5-(2-phenylethyl)-7-(phenylmethylene)-2-(2,2,2-trifluoromethyl)-2H-pyrazolo-[4,3-c]pyridine, meleate (1:1).

* * * * *